United States Patent
Feldman (10) Patent No.: US 6,543,936 B2
(45) Date of Patent: Apr. 8, 2003

(54) APPARATUS FOR DIAGNOSIS AND/OR TREATMENT IN THE FIELD OF DENTISTRY USING FLUOROSCOPIC AND CONVENTIONAL RADIOGRAPHY

(76) Inventor: Daniel Uzbelger Feldman, c/o Bolet & Terrero. Av. Fco. de Miranda, Edif. Cavendes, piso 12, Los Palos Grandes, Caracas 1062 (VE)

(*) Notice: Subject to any disclaimer, the term of this patent is extended or adjusted under 35 U.S.C. 154(b) by 3 days.

(21) Appl. No.: 09/841,346

(22) Filed: Apr. 24, 2001

(65) Prior Publication Data

US 2002/0154742 A1 Oct. 24, 2002

(51) Int. Cl.⁷ .................................................. G21K 4/00
(52) U.S. Cl. ...................................... 378/191; 378/98.8
(58) Field of Search ................................ 378/191, 98.8, 378/197

(56) References Cited

U.S. PATENT DOCUMENTS

| | | | |
|---|---|---|---|
| 3,622,785 A | * 11/1971 | Irwin | ......................... 378/191 |
| 4,142,101 A | 2/1979 | Yin | |
| 4,160,997 A | 7/1979 | Schwartz | |
| 4,188,537 A | 2/1980 | Franke | |
| 4,409,616 A | 10/1983 | Ledley | |
| 4,593,400 A | 6/1986 | Mouyen | |
| 4,829,548 A | 5/1989 | Halm et al. | |
| 4,979,198 A | 12/1990 | Malcolm et al. | |
| 5,331,166 A | * 7/1994 | Yamamoto et al. | ......... 378/191 |
| 5,434,418 A | 7/1995 | Schick | |
| 5,510,623 A | 4/1996 | Sayag et al. | |
| 6,236,712 B1 | * 5/2001 | Tomasetti | .................... 378/114 |

* cited by examiner

*Primary Examiner*—Craig E. Church
(74) *Attorney, Agent, or Firm*—Ladas & Parry (57) ABSTRACT

An apparatus for use in the field of dentistry consisting of a rotatable c-arm assembly having a housing with an emitter on one end and a fluoroscopic image receptor at another end, a control panel, three mechanical arms connecting the housing and the control panel to each other, an intraoral image receptor and a plastic holder device for the intraoral image receptor. The apparatus has the improved feature of having two modes of operation, a fluoroscopic mode or a conventional radiographic mode. The mode of operation is selected by the operator by a foot pedal for use in fluoroscopic mode, or a hand activator control for use in conventional mode. A beam of x-rays or gamma rays is emitted from the housing corresponding to the selected mode. The beam is incident on the fluoroscopic image receptor or on the intraoral image receptor and the image is converted to visible light, amplified and transmitted to a computer monitor and/or television set and VCR, thus allowing the observation of dental procedures in real time.

20 Claims, 7 Drawing Sheets

APPARATUS FOR DIAGNOSIS AND/OR TREATMENT IN THE FIELD OF DENTISTRY USING FLUOROSCOPIC AND CONVENTIONAL RADIOGRAPHY

BACKGROUND OF THE INVENTION

1. Field of the Invention

The present invention relates generally to the field of diagnostic radiology, and specifically to an improved apparatus that operates in both the conventional radiographic mode and in the fluoroscopic mode in order to observe and record any dental procedure in all areas of dentistry in any region of the mouth, and the method of using the same. This improved apparatus and method allow for the efficient execution of dental radiographs in static time and in real time, by providing a rotating and folding adjustable C-arm assembly as well as a plastic support for an intraoral image receptor, said plastic support securely holds the receptor in place and yet can be easily manipulated so as to decrease operating time and allow freedom of movement, thus improving operating efficiency.

2. Description of the Related Art

Before the discovery of electromagnetic radiation known as x-rays, techniques and procedures in the field of dentistry were based on purely empirical knowledge. On Nov. 8, 1895, William Conrad Roentgen announced the discovery of this new kind of radiation. Within fourteen days, Otto Walkhoff, a German dentist, took the first dental radiograph of his own mouth. Dr. William James had completed several dental radiographs five months later. In 1896, William Herbert Rollings created an x-ray device specifically for dental use. In 1913, Coolidge improved the manufacturing techniques of the x-ray tube, which allowed for better control of the quality and quantity of radiographs. The panoramic x-ray device was invented in 1950.

All of these innovations allowed the dentist to be able to observe for the first time areas of the mouth, such as under the gums, and evaluate the use of specific dental treatments. Over the past few years, the traditional x-ray device has been modified by the use of computers, specifically a programmed computer receptor, known as CDR (Computed Digital Radiography), which eliminates the disadvantage of extensive developing and exposure time required of the older x-ray device. Some of the principles of this kind of technology are described in Pat. No. 4,188,537 of Franke, 1980, Pat. No. 4,593,400 of Mouyen, 1986, Pat. No. 4,829,548 of Hahn et al., 1989, Pat. No. 5,434,418 of Schick, 1995 and Pat. No. 5,510,623 of Sayag, 1996. One of the disadvantages of these conventional radiographs with CDR is that the images provided are in static time. The fluoroscope, an apparatus consisting of an x-ray tube and a fluorescent screen, provides visible images in real time. Images produced by the invisible radiation of x-rays or gamma rays, are transformed to visible images when reacting with phosphor in the screen. Despite such advantage, the fluoroscope has not been used in the field of dentistry to carry out routine treatments such as removal of cavities, extraction of third molars, root canal system treatments, placement of dental implants, reduction of maxillary fractures and generally, for procedures wherein the use of x-rays is necessary.

Up until now, there has not been described an apparatus, designed specifically for dental use, that: allows the user to see and/or record, in a computer monitor and/or in a television set and VCR, a dental procedure as the procedure is being performed; allows for use of conventional radiography as well as fluoroscopic radiography; includes an intraoral image receptor with a plastic structure that provides durable support and can be easily manipulated; and enhances versatility of use and function by providing a portable, adjustable design that fulfills international regulations as to radiological protection.

BRIEF SUMMARY OF THE INVENTION

In accordance with the present invention, the apparatus consists of a dual imaging device comprising a housing, a C-arm assembly, a fluoroscopic image receptor, an intraoral image receptor, a plastic holder device and a control panel; said housing having an emitter containing an x-ray tube; said C-arm assembly being connected at one end to said housing assembly and being connected at the other end to said fluoroscopic image receptor; said fluoroscopic image receptor and said intraoral image receptor having fluorescent screens; said plastic holder device holding said intraoral image receptor in position; said control panel having dual digital controls for operation of the apparatus in conventional and/or fluoroscopic radiography.

OBJECTS OF THE INVENTION

The principle objective of this invention is to introduce in the field of dentistry, an improved apparatus able to convert the invisible radiation emitted by an x-rays or gamma rays origin source, going through a dental region of a patient, into a visible light image. The apparatus contains two receptors, both of which convert the emissions through the use of a fluorescent screen. One fluoroscopic image receptor is located at an end of a c-arm assembly. The other image receptor is an intraoral image receptor which is supported by a plastic device. The image of visible light is transmitted by a fiber optic cone, fiber optic plate and/or by a fiber optic cable, then amplified by an image intensifier, converted into a video signal by a charge coupled device (CCD) and sent by a 75 Ohm cable or other video connector to a computer monitor and/or television set and VCR. This allows the observation and/or recording of the dental diagnosis and/or procedure in real time, not only in static time, thus saving time for the operator and reducing mistakes previously made during administration of dental treatments, providing better service, comfort and security for the patient. This improved apparatus also provides efficient operation in two modes of use, a conventional radiographic mode and a fluoroscopic mode. The apparatus is a little, light and economic device specifically adapted as a tool for diagnosis and treatment in the field of dentistry.

DETAILED DESCRIPTION OF THE INVENTION

Figure 1:
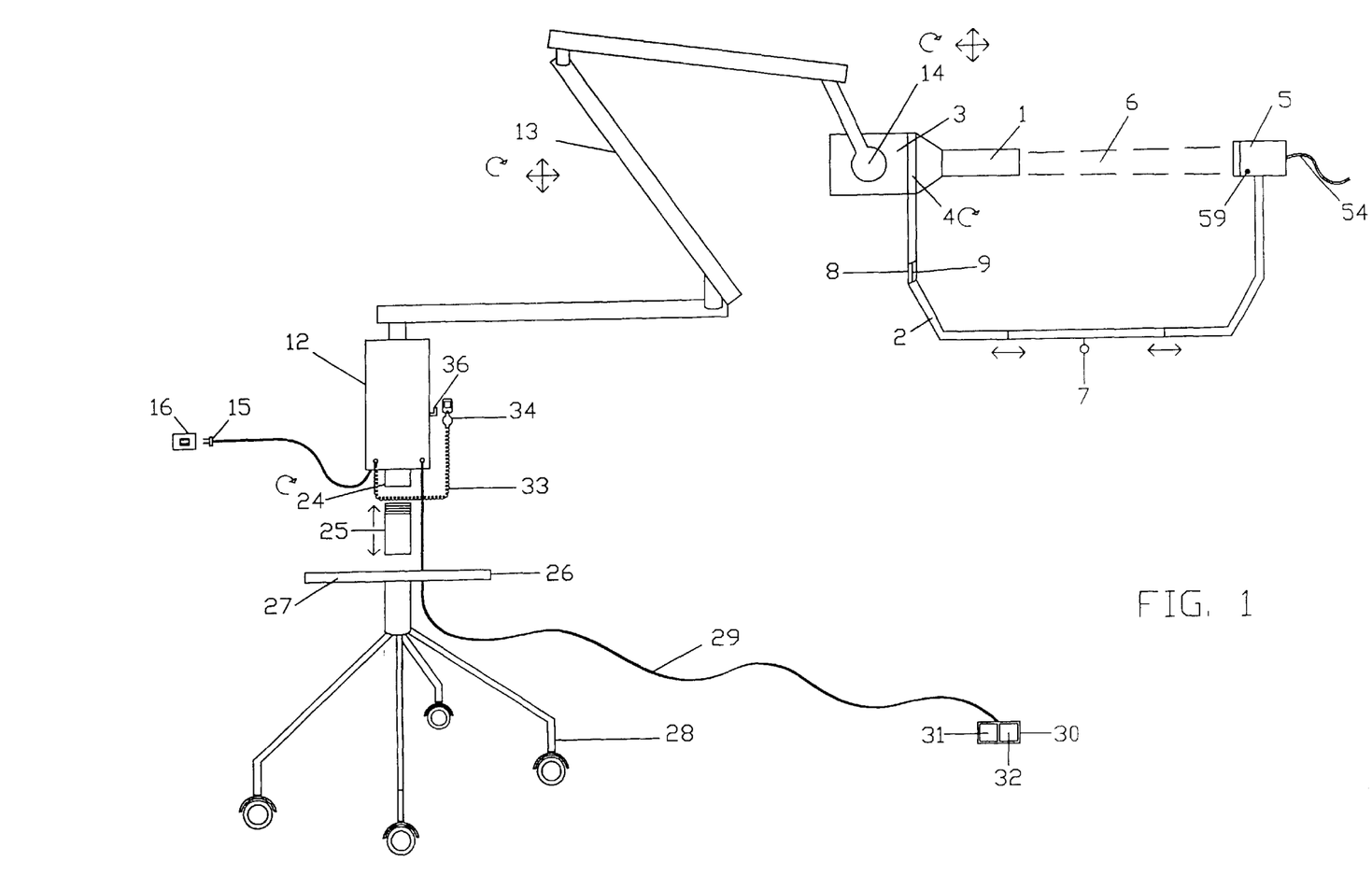
FIG. 1 is a side schematic view of the configuration of the system and a front perspective of the control box following the principles of the herein invention.
Figure 4:
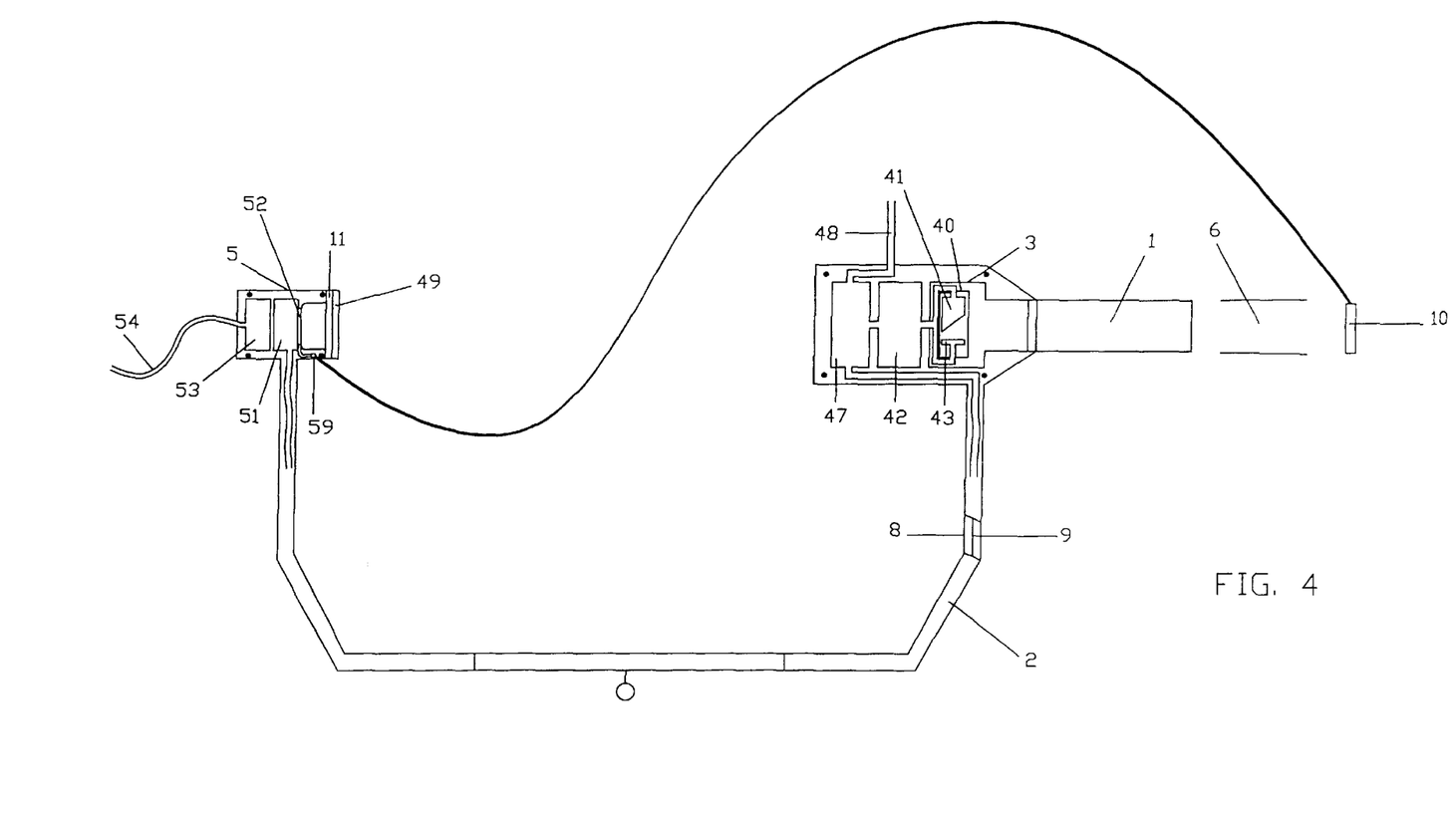
FIG. 4 is a side schematic view of the device of FIG. 1, showing the intraoral image receptor.

Referring to FIGS. 1 and 4, there is shown apparatus according to the invention for producing real time images of a dental region of a patient.

The apparatus comprises an emitter 1 capable of producing x-rays or gamma rays to be passed through the dental region of the patient under examination. The emitter 1 is supported at one end of a C-arm assembly 2 and is mounted for rotation by a joint 4 about an axis of a housing 3 of an x-rays radiation source. The emitter faces a fluoroscopic image receptor assembly 5 which is supported at an opposite end of the C-arm assembly 2. A radiation beam 6 is emitted by emitter 1 and directed into the fluoroscopic image receptor assembly 5. The C-arm assembly 2 which is rotatable around the axis of housing 3 can be placed into a position in which the dental region of the patient to be examined will be directly in the radiation beam 6.

Figure 3:
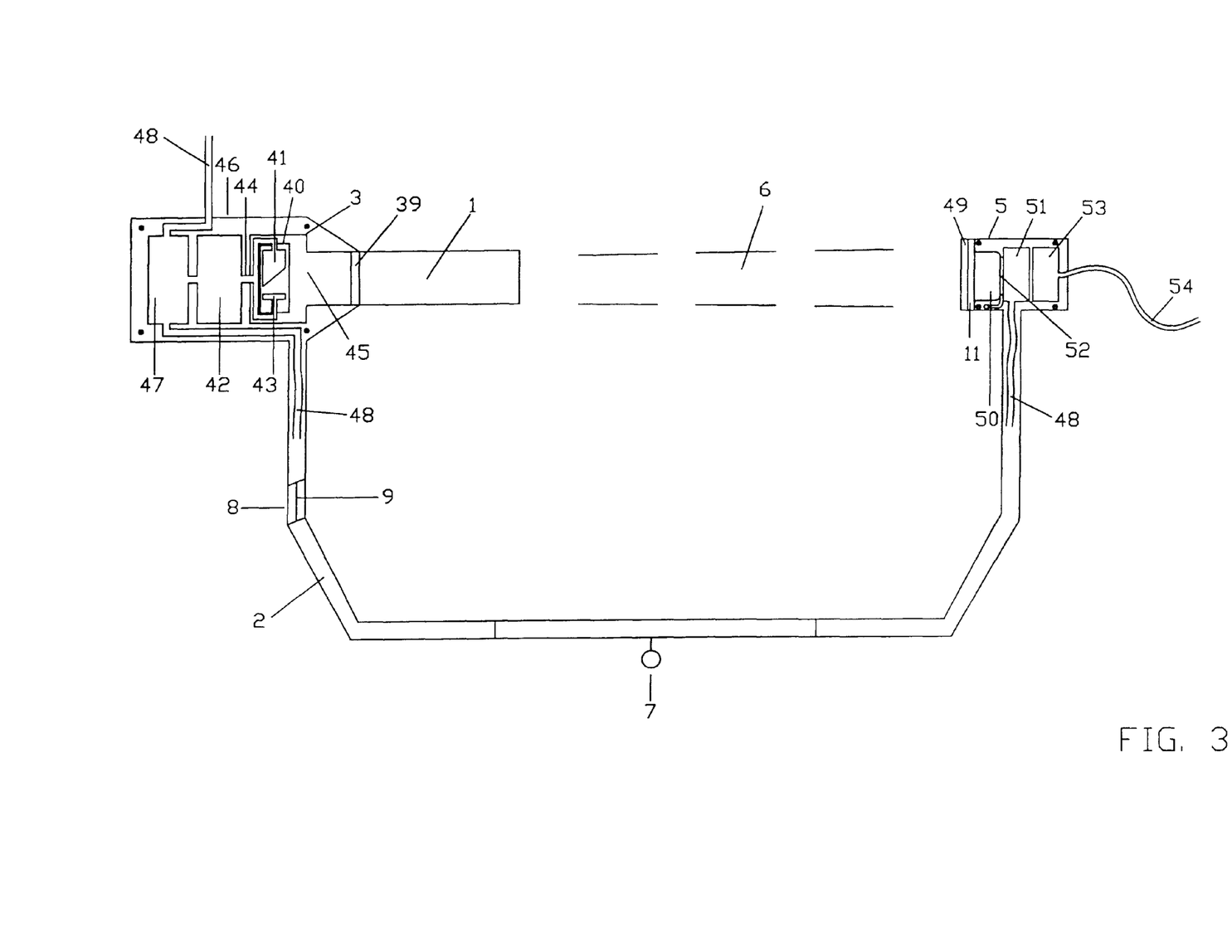
FIG. 3 is a side schematic view of the device of FIG. 1, showing most of the components of the c-arm assembly.

The C-arm assembly 2 has a telescopic, straight section extending parallel to beam 6 and including a lockable member 7 to fix the distance between emitter 1 and receptor assembly 5. Thereby, the C-arm assembly can be adjusted to take into account the size of the patient, the angle of the beam and the focal distance of assembly 5. The C-arm assembly 2, as seen in FIG. 3, has a hinge 8 with a hinge lock 9, that allows for the assembly to be folded with respect to housing 3 in order to avoid an overlapping or distortion of the image obtained when using the intraoral image receptor 10. This C-arm assembly, with all its components and parts, is attached to a control panel 12 through three mechanical arms 13, with a length from 70 centimeters to 1 meter each, that are able to extend, fold, move up, down, right and left. These three mechanical arms 13 are connected to each other, one arm connected at one end to the upper part of the control panel 12, another arm connected at one end to the side of the housing 3.

Housing 3 is connected to the mechanical arm via a spin attachment 14 which allows movement of the housing in four directions.

Figure 2:
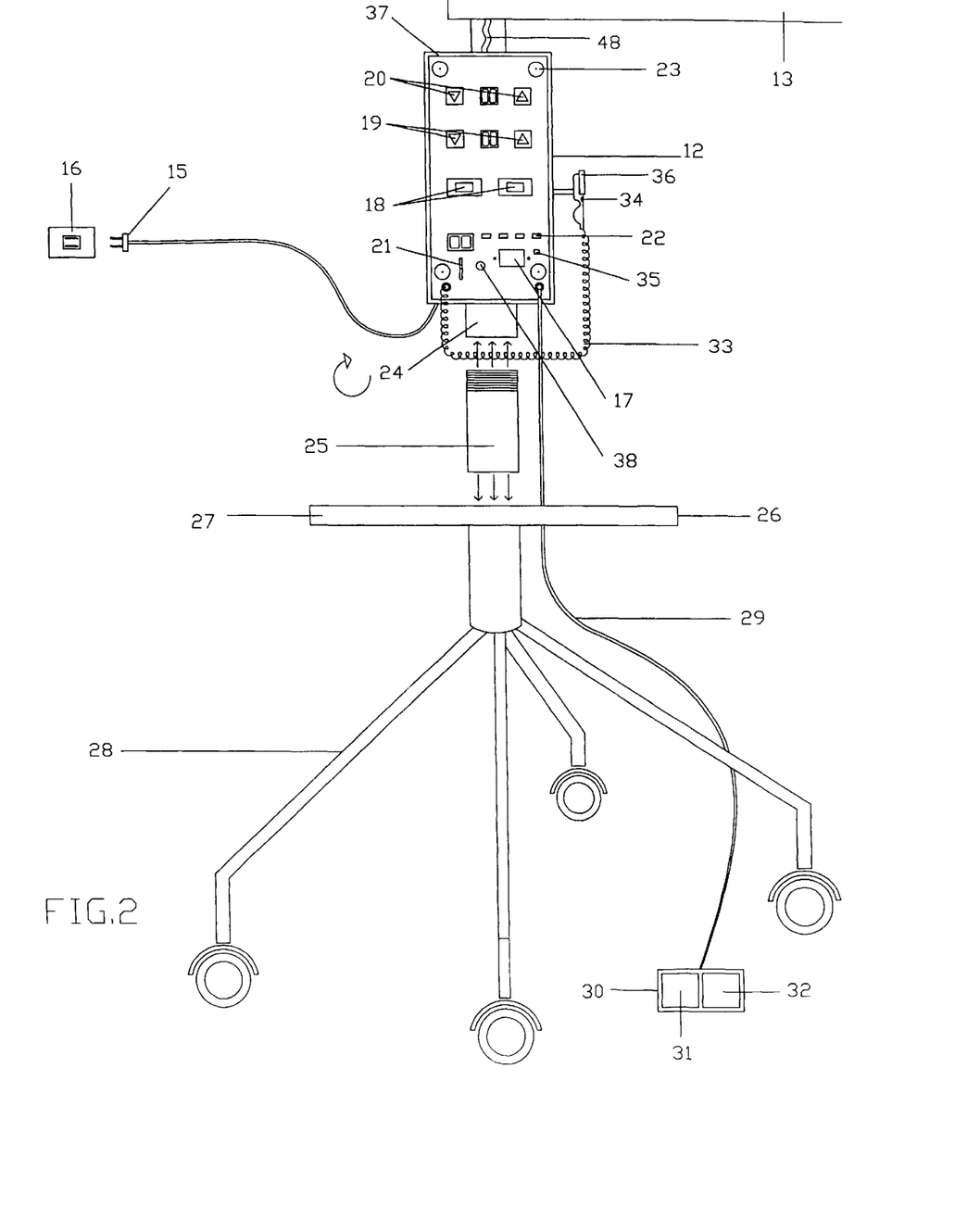
FIG. 2 is a front view of the versatile control box, showing most of the different selection commands and their components according to the principles of the invention.

In FIGS. 1 and 2 there is shown the system activating controls. The control panel 12, that is connected to the power supply 15 by outlet 16, has an on/off switch 17, digital controls 18 for activation of both modes of operation, kilovoltage level control 19, amperage level control 20, exposure timing circuits 21 and exposure time alarm control 22, having a visible and auditory signal. The control panel 12 has the versatility of being able to be fixed on a wall by four wall screws 23 or of being portable by use of an attachment tube 24 which is screwed to an attachment device 25 and inserted into a portable table 26, said table having a flat surface comprised of a lead weight 27 and four legs with four wheels 28 for mobility. The mechanical arms 13 can be installed in the roof or ceiling (not shown) of a dental office, and connected to control panel 12 by means of a cable, when control panel 12 is installed on a wall. Control panel 12 comprises a pedal cable 29 and a pedal 30, pedal 30 having a pedal control 31 for activation of the device in fluoroscopic mode and a pedal control 32 for activating recording of procedures in a computer program or VCR. Control panel 12 also comprises a hand control cable 33, with hand activator control 34 which activates the emission of radiation in the conventional mode. Both pedal 30 and hand activator control 34 may be activated and connected to panel 12 by other means, such as through infrared devices or sensors 35. At the left side of panel 12, there is a plastic holder 36 that can be used for holding hand activator control 34. Inside control panel 12 there is a microprocessor control system 37 for execution of the system controls, producing an audio signal of the system conditions, and also providing an LCD panel 38 which is illuminated from its back side to provide the operator better visibility of the system conditions.

In FIG. 3, the components which constitute the housing 3 and the fluoroscopic image receptor assembly 5 are shown. In fluoroscopic operation mode, the spreading of the emitted radiation beam 6 is reduced by the addition of a beam limiter 39 to emitter 1, thus causing beam 6 to effectively react with assembly 5 thereby avoiding unnecessary exposure of radiation to the operator. Housing 3 is joined to emitter 1 and beam limiter 39. A window 45, of the same size as the outlet of emitter 1, is provided in housing 3. Inside housing 3, the x-rays or gamma rays generating source is placed. It may be a radioactive source, a radiation generator, a gamma rays source, charged particles radiation, neutral particles radiation, a Marx generator and an x-rays tube or a little x-rays tube 40 of the Eureka EXR-80-20D type which anode 41 is precisely located in the axis of the emitter 1. The x-rays tube is filled with oil as isolator and surrounded by isolators of electric materials of the Kapton or Stycast 2850-FT type. The high voltage power source 42, feeding the x-rays tube cathode 43 by a high voltage connector assembly 44, is surrounded by a lead shield of 1 millimeter of thickness at the side of cathode 43, reducing in thickness to 0.15 millimeters around the assembly 44. A low voltage electronic power amplifying system 47 is located next to high voltage power source 42. Amplifying system 47 is connected by low voltage cable 48 to the microprocessor 37. The material of housing 3 is preferably aluminum of 0.5 millimeters of thickness which, along with the oil and the other isolating materials, provides the filtration necessary to keep the quality of the radiation beam 6. The housing 3 may be covered with a plastic or lead plastic cover 46, in order to protect the operator and the patient from radiation dispersion, as well as to provide an aesthetic appearance. The high voltage power source 42 is located on the opposite side of assembly 44, as compared to the x-rays tube, in order to reduce filtration of high voltage and the problems associated with transmission and interference of electrical flow.

To use the system in the conventional mode, the appropriate button in digital control 18 is pressed. Once this mode is selected, the voltage peaks will be automatically within a range of 35 to 80 kilovolts and a milliamperage between 3 and 10 milliampers. Thereafter, there is placed inside the mouth of the patient in the selected place, a periapical dental radiography, infant periapical, occlusal or coronal with a bit flap. Emitter 1 is aimed in the direction of the radiographic film at a pre-established angle and the device is activated with hand activator control 34. When executing this action, high voltage power source 42 is activated, which makes the electrons going through the x-rays tube cathode 43 circulate to the anode 41 in one direction, forming radiation beam 6 which flows out of emitter 1 and affects the film after going through the tissues of the individual to be examined. Thereafter, the radiograph is developed following the instructions of the manufacturer. The radiation beam 6 is directed for an interval of time that may vary from 0.01 seconds to 4 seconds. Respecting all the international regulations of radiological protection, the radiation doses produced by the device does not exceed 3 mrem.

To use the system in fluoroscopic mode, the appropriate button in digital control 18 is pressed. With this mode of operation selected, voltage peaks will be within a range of 40 to 75 kilovolts and a microamperage between 50 to 300 microamperes. The operator places the emitter in the dental region of the patient to be examined, thereafter pressing pedal control 31 for activation of the mode and pedal control 32 for recording. This activates amplifying system 47 to produce an energy flow that stimulates production in high voltage power 42 of electron flow in anode 41, thus producing a radiation beam 6 whose quality corresponds to the kilovoltage and microamperage selected levels. As shown, the incidence of radiation beam 6, after its emission from the x-rays source and after passing through the individual examined, arrives to an optically opaque but transparent window 49 located in front of the image receptor assembly 5. This transparent window 49 may be manufactured of a black plastic material such as Derlin, with a thickness of 1 millimeter. At its back there is the high resolution x-ray/gamma ray sensitive fluorescent screen 11, made of Colutron P43, Kodak Lanex or of a similar material, which functions with very low levels of radiation, within a range of 0.15 Roentgen/min to 2 Roentgen/min, to convert the invisible defined image of the x-rays into an optically visible image of a very low density. The visible light produced directly contacts a fiber optic cone or plate assembly 50, such as Schoott 73A, Phillips SQ053 or INCOM MEGA draw MDL, which transmits this low density visible light image to an image amplifier assembly 51, such as Proxitronic Proxifier BV-40, which is connected to low voltage electronic power amplifying system 47 or to an integrated power supply that allows a high amplification of the visible light. Between the fiber optic assembly 50 and the image amplifier assembly 51, there may be interposed optical lenses 52 if it is desired to minimize or magnify the obtained image. The image amplifier assembly 51 keeps a high resolution of the image obtained, on the order of 80 Line Paris/mm, and is capable of multiplying by 1000 times, electron by electron, the intensity of the light of the image produced by the high resolution sensitive screen 11, thus allowing reduction by 75% of radiation doses received by the patient and operator. The image amplifier assembly 51 produces a visible brilliant image that arrives to a charge coupled device 53, which may be a CCD sensor array such as Marconi CCD05-30 or Philphs FTT 1010-M, a CCD camera such as Plunix DN 0007 or Sony ICX024/ICX022 or ICX083/ICX082, or a camera tube such as the Vidicon standard or Plumbicom XQ2182/03X type, that produces a high resolution without delay of the image, which is sent by a 75 Ohm cable 54 or by any other video connector to a computer monitor and/or television set and VCR, which allows the observation and/or recording of diagnosis and/or dental procedures performed on the patient in real time, that is, while such are taking place.

Figure 5:
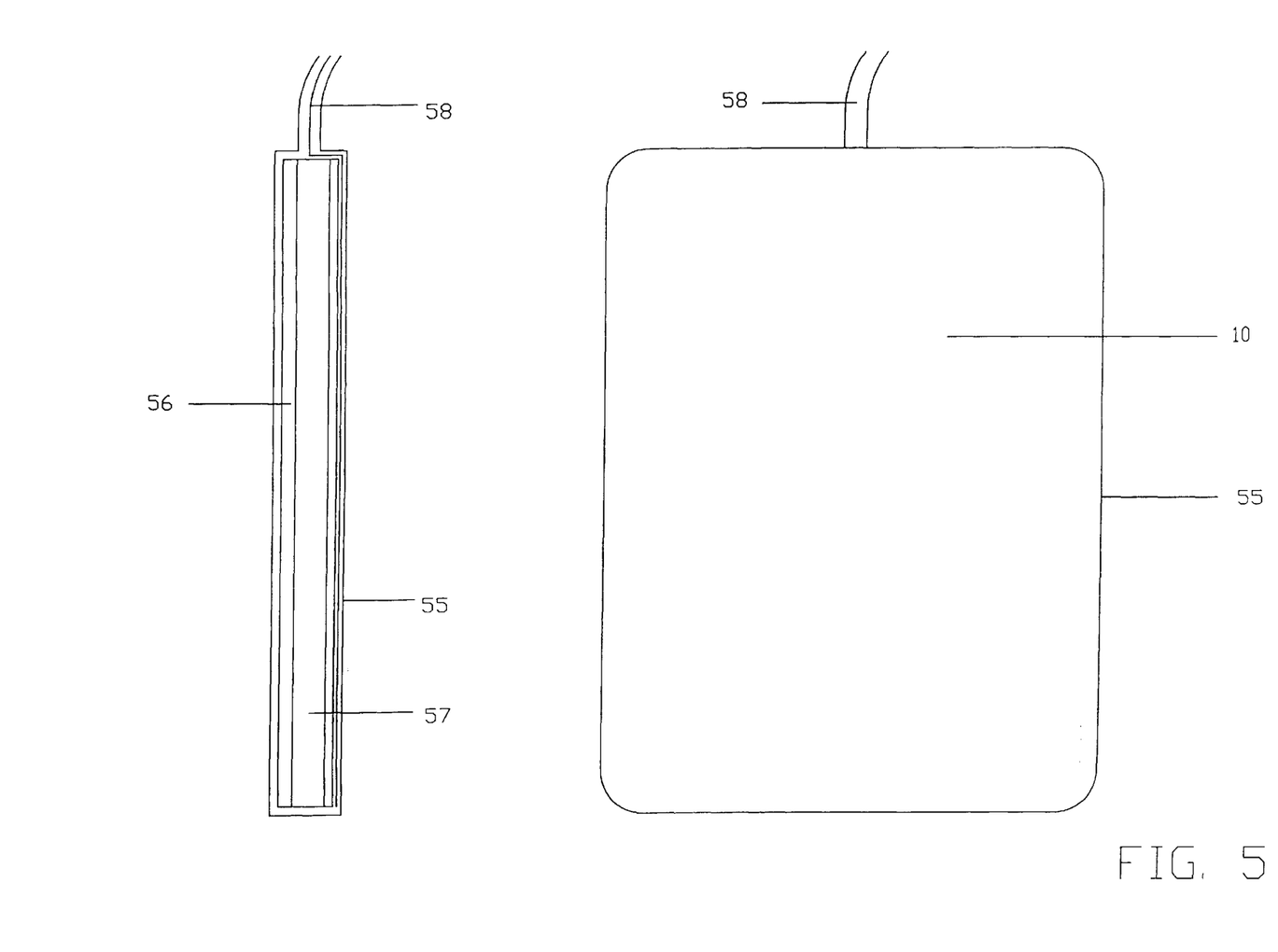
FIG. 5 is a side and front sectional view of the intraoral image receptor, showing the position of most of it's components.
Figure 6:
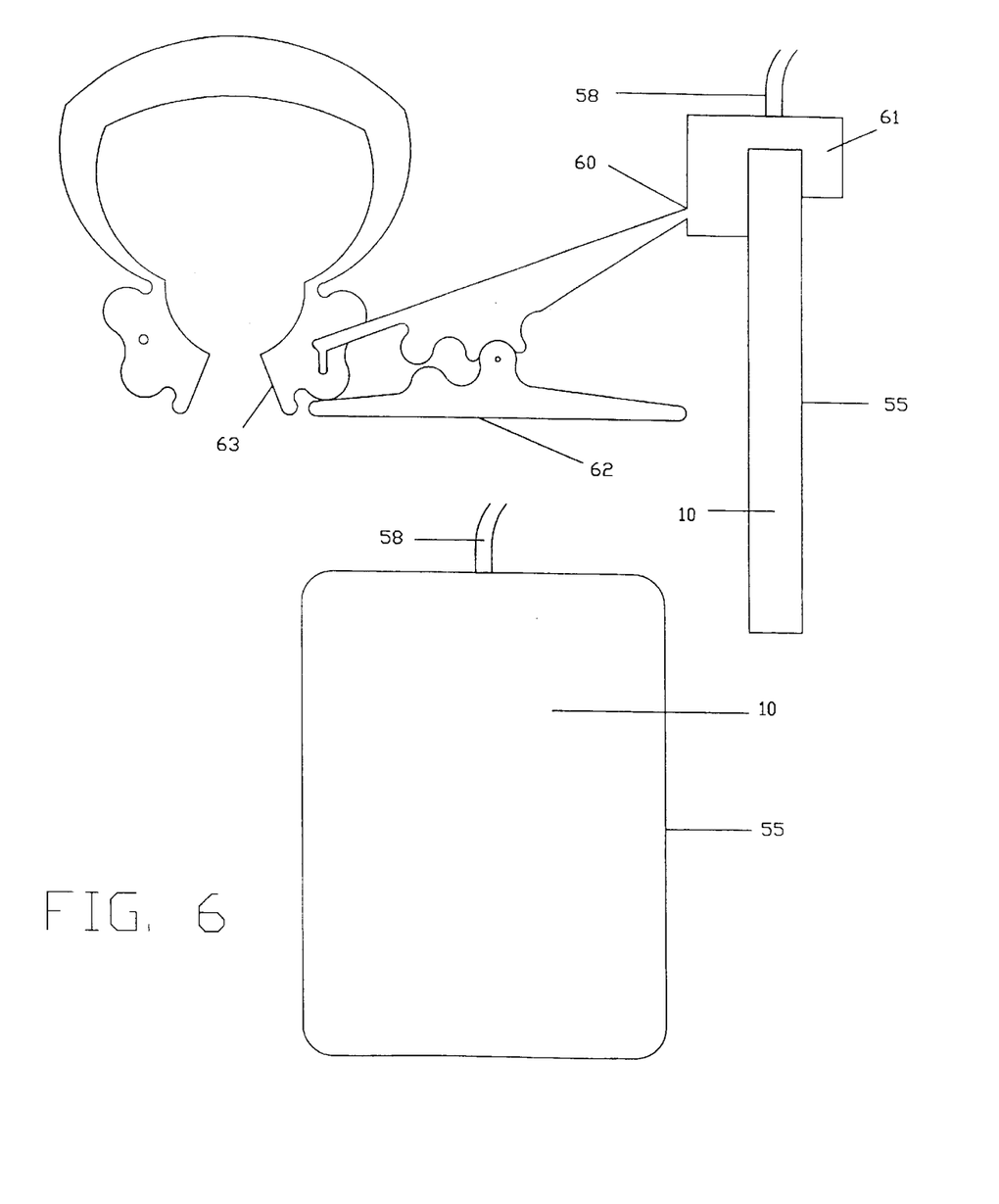
FIG. 6 is a side and front view of the intraoral image receptor, showing the plastic support device which can be used with an endodontic clamp.

In FIGS. 4 and 5 there is shown an intraoral image receptor 10, specifically designed for executing dental procedures involved in a root canal system treatment, which functions with voltage peaks within a range of 40 to 75 kilovolts and a microamperage between 50 to 300 microamperes. The operator leads emitter 1 to the dental region of the patient to be examined, activates pedal control 31 and immediately the low voltage electronic power amplifying system 47 is activated, producing a low energy flow that stimulates the production in high voltage power 42, connected to cathode 43, of electron flow, producing at anode 41, a beam 6 of low energy that affects the intraoral image receptor 10. The intraoral image receptor 10 includes a lead foil backing 55 that helps to reduce radiation exposure to the patient, and has the further advantage of not allowing the passage of visible light through its fore face while allowing the passage of x-rays. Lead foil backing 55 has a total thickness of approximately 1 millimeter. The intraoral image receptor 10 contains a small fluorescent screen 56 which converts the invisible radiation emitted by the origin source into a visible light image of low intensity. The small fluorescent screen 56, which may be 40 millimeters in height by 30 millimeters in width for an adult patient and 30 millimeters in height by 20 millimeters in width for a child patient, can be a screen such as the Proxitronic P43, comprised of a thin base of indium tin oxide, a chromium ring, a phosphor layer and an aluminum reflecting layer. This small fluorescent screen 56 with a thickness of 60 microns sends the image to a fiber optic plate coupling 57, such as the Schott 47ARH, that may be 40 millimeters in height by 30 millimeters in width for an adult patient and 30 millimeters in height by 20 millimeters in width for an child patient, and with a thickness of 3 millimeters. Coupling 57 contains a glass core that increases its resistance to radiation, allowing it to support intensities up to 100 rads. It transmits the image, through a fiber optic cable 58 to fiber optic connector 59, and then to image amplifier 51, which transforms it into a visible brilliant image. Image amplifier assembly 51, connected to charge coupled device 53, converts the image into a high resolution video signal and transmits via 75 Ohm cable 54 or another video connector to a computer monitor and/or television or VCR, which allows the observation and/or recording of the procedure in real time. The total thickness of the intraoral image receptor 10 may be close to 4 millimeters in its totality, including all its components, and may be manufactured in any size pursuant to the region to be radiographed or for use in the intended dental specialty. When the intraoral image receptor 10 is used, the C-arm assembly 2 may be folded through hinge 8 by opening hinge lock 9, so as to prevent an overlapping or distortion of the image obtained. For keeping the intraoral image receptor 10 inside the mouth of the patient while endodontic procedures are taking place and to prevent a time loss caused by inserting or removing the intraoral image receptor 10 every time a procedure is to be observed, there is provided a plastic holder device 60. Plastic holder 60 surrounds the intraoral image receptor 10 by means of an intraoral image receptor holder 61 and clip 62 which securely hold receptor 10 in the flap of an endodontic clamp 63 that is used routinely for the execution of root canal system treatments. To fulfill health and sterilization regulations, the intraoral image receptor 10 and part of the fiber optic cable 58 must be covered by any of the sterile transparent plastic protectors existing in the market for these purposes, which are discarded and changed from one patient to another.

If it is wished to use the apparatus as a CDR device, as noted in FIGS. 1, 2, 3 and 4, it may be disregarded of the conventional radiographic film, and the expositions to the radiation may be made after going through the subject being examined, directly over the fluoroscopic receptor image assembly 5 of the C-arm assembly 2 or over the intraoral image receptor 10, in order to achieve the observation and/or recording of the image in a computer monitor and/or VCR in static time only, for these purposes, there must be selected in the control panel 12 in the exposure timing circuits 21, a range between 0.01 seconds to 0.10 seconds that are started by a hand activator control 34 when selecting the fluoroscopic mode.

Figure 7:
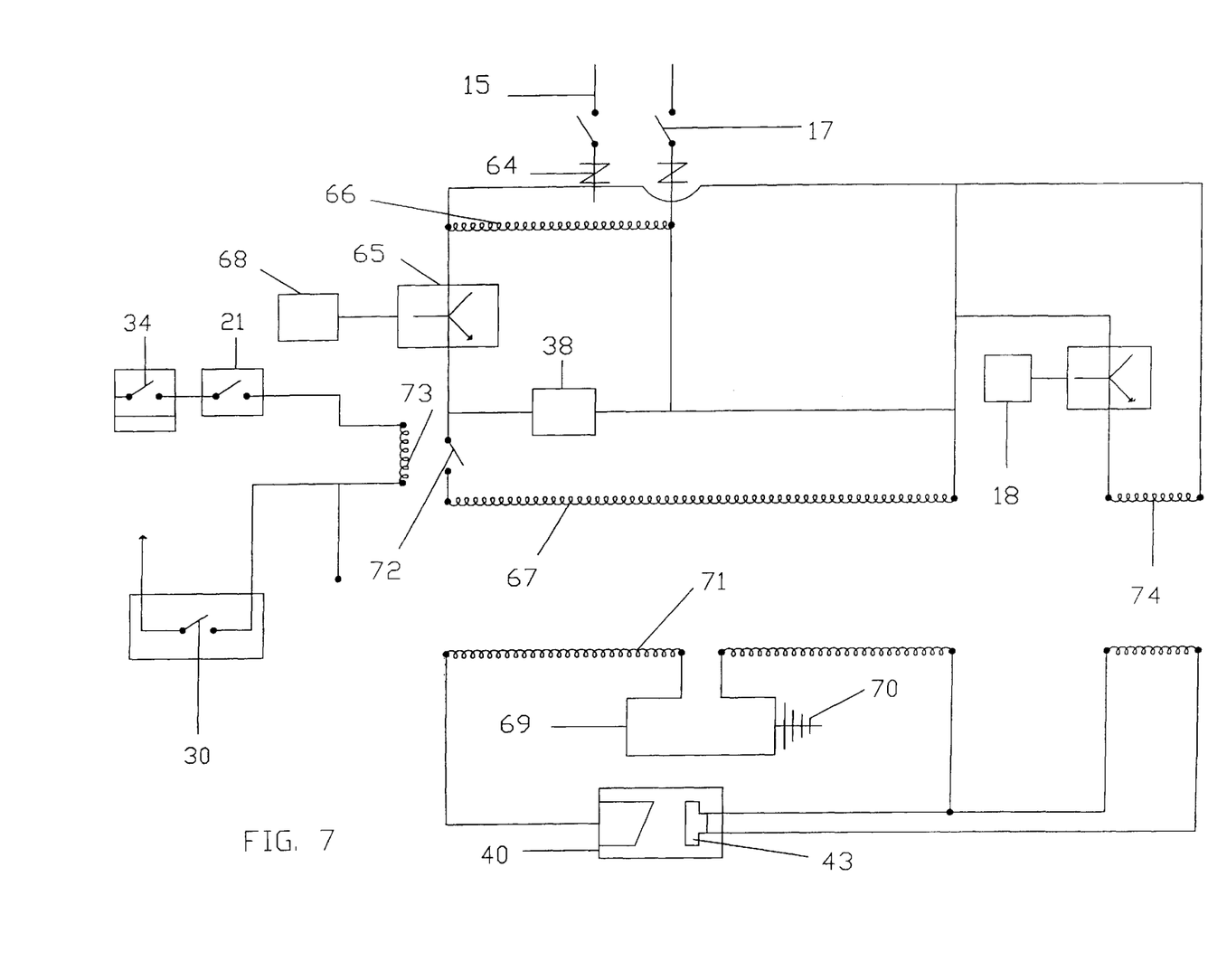
FIG. 7 is a diagram of the general characteristics of the electric circuit according to the principles of the invention.

In FIG. 7, a diagram of the general features of the electric circuit of the invention is shown. The circuit will be connected to power supply 15 by a main switch of the on/off switch 17, which is protected by fuses 64. The controls are provided with transistors with analogic-digital interfaces 65 for handling the selected digital function. The autotransformer 66 provides the power difference for the principal transformer 67 that may contain a nine turns cooper wire. This power difference is measured by a digital voltmeter 68 in kilovolts, gauged for indicating the power being applied to the x-rays tube 40. Ground circuit 70 in secondary transformer 71 has a digital ampmeter 69 that may contain a cooper wire with 3200 turns in five isolated segments, and measures the electric flow that goes through the x-rays tube 40. The x-rays switch 72 is part of the relay circuit 73, which is controlled by pedal 30, or by exposure timing circuits 21 for hand activating control 34. These are connected to the display panel 38 for signaling the activity of the system. The electric flow for the filament in cathode 43 comes from filament transformer 74 and varies according to the mode of operation 18 selected by the operator.

In order to reduce the level of exposure to radiation of the patient and operator, it is customary to use mechanical barriers of radiological protection. To fulfill the regulations of the Federal Food and Drug Administration (FDA), auditory warning alarms must indicate when levels of exposure exceed the limit of 5 R/min. According to the Guidance of Dose Levels for the Radiography Diagnostic for a typical adult patient of the Atomic Energy International Agency, Vienna 1994 (IAEA), the allowed doses for the periapical dental radiograph are 7 mGy. In conventional radiographic mode, following the principles of the invention, the dosages are lower than 3 mrem, within the limits established by the IAEA for the periapical dental radiograph. According to the Dose Rate Guidance Levels for Fluoroscopic use for a Typical Adult Patient of the IAEA, Vienna 1994, the doses allowed in normal fluoroscopic operation mode are up to 25 mGy/min. In the fluoroscopic mode, following the principles of this invention, dosages vary from 0.15 R/minute to 2 R/minute, also within the limits established by the IAEA for fluoroscopic use.

It is to be understood that the above described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. Apparatus for use in dentistry for producing real time fluoroscopic images, said apparatus comprising:
    a housing for emitting x-rays or gamma rays for passage through a dental region of a patient;
    an image receptor assembly comprising a fluoroscopic image receptor positioned to receive the x-rays or gamma rays after passage thereof through the dental region of the patient to produce a visible light image of said dental region, a fiber optic system connected to said image receptor to transmit the light image, a charge coupled device connected to said fiber optic system to produce a high resolution video signal from said light image;
    a rotatable C-arm assembly for holding said housing and said image receptor assembly;
    a control panel for controlling and observing operation of the apparatus;
    three mechanical arms connecting said housing and said control panel;
    an intraoral image receptor that can be positioned to receive the x-rays or gamma rays after passage thereof through the dental region of the patient;
    a plastic holder device for positioning said intraoral image receptor; and
    a monitor for receiving said video signal to display in real time the dental region of the patient.

2. The apparatus as claimed in claim 1, wherein said C-arm assembly comprises said housing at one end and said fluoroscopic image receptor at an opposed end; said C-arm assembly comprising a telescopic straight section to vary a distance of said one end of the C-arm assembly relative to said other end; said straight section including a lock for locking said telescopic section once a distance is selected; said one end of said C-arm assembly including a hinge and a hinge lock.

3. The apparatus as claimed in claim 2, wherein said housing comprises a window at one end, an emitter positioned next to said window, said emitter including a beam limiter, an x-ray tube including an anode and a cathode, a high voltage power source feeding said x-ray tube through a high voltage connector assembly, an electronic power amplifying system positioned next to said high voltage power source, electronic power amplifying system connected by a low voltage cable to said control panel, and a protective lead plastic cover surrounding said housing.

4. The apparatus as claimed in claim 3, wherein said image receptor assembly further comprises a window at one end, said window positioned to allow passage of said x-rays to said fluoroscopic image receptor, an image amplifier assembly which receives the transmitted light image from said fiber optic system, optical lenses interposed between said fiber optic system and said image amplifier assembly, a cable which transmits said video signal from said charge coupled device to a computer monitor and/or television and VCR, and a fiber optic connector which receives an image from said intraoral image receptor.

5. The apparatus as claimed in claim 4, wherein said control panel comprises a housing including a microprocessor, said microprocessor connected to an on/off switch, digital controls, a kilovoltage level control, an amperage level control, exposure timing circuits, exposure time alarm control including visual and auditory signals, and a LCD panel, said housing including a pedal cable, a hand control cable, and a power supply emerging therefrom, said pedal cable including an activator pedal for use in fluoroscopic mode, said hand control cable including a hand activator control for use in conventional radiographic mode, said housing including a plastic holder for holding said hand control cable when not in use.

6. The apparatus as claimed in claim 5, wherein said control panel housing is connected to a wall by four screws.

7. The apparatus as claimed in claim 5, wherein said control panel housing comprises an attachment tube connected to an attachment device, said attachment device connects to a portable table which includes a lead weight for balance and four legs having four wheels for portability of said control panel.

8. The apparatus as claimed in claim 6, wherein said activator pedel has two pedal controls, one for activation of said apparatus in fluoroscopic mode, another for activation of recording of a procedure.

9. The apparatus as claimed in claim 8, wherein one arm of said three mechanical arms is connected to said control panel, another arm of said three mechanical arms is connected to said housing, wherein said three mechanical arms are connected to each other; said mechanical arms being able to extend, fold and move in various directions.

10. The apparatus as claimed in claim 9, wherein said intraoral image receptor comprises a fluorescent screen at one end which receives said x-rays after passage through the dental region of the patient, a fiber optic plate coupling which receives an image from said fluorescent screen, a fiber optic cable which transmits said image to said fiber optic connector of said image receptor assembly, and a lead foil backing positioned at an opposed end, in relation to said fluorescent screen, to reduce radiation exposure to the patient.

11. The apparatus as claimed in claim 10, wherein said plastic holder device comprises an intraoral image receptor holder and a clip.

12. Apparatus for use in dentistry for producing real time fluoroscopic images, said apparatus comprising:

a housing for emitting x-rays for passage through a dental region of patient, said housing comprises a window at one end, an emitter positioned next to said window, said emitter including a beam limiter, an x-ray tube including an anode and a cathode, a high voltage power source feeding said x-ray tube through a high voltage connector assembly, an electronic power amplifying system positioned next to said high voltage power source, said electronic power amplifying system connected by a low voltage cable to said control panel, and a protective lead plastic cover surrounding said housing;

an image receptor assembly comprising a fluoroscopic image receptor positioned to receive the x-rays or gamma rays after passage thereof through the dental region of the patient to produce a visible light image of said dental region, a window at one end, said window positioned to allow passage of said x-rays to said fluoroscopic image receptor, a fiber optic system connected to said image receptor to transmit the light image to an image amplifier assembly, optical lenses interposed between said fiber optic system and said image amplifier assembly, a charge coupled device connected to said fiber optic system to produce a high resolution video signal from said light image; a cable which transmits said video signal from said charge coupled device to a computer monitor and/or television and VCR, and a fiber optic connector which receives an image from an intraoral image receptor;

a rotatable C-arm assembly comprising said housing at one end and said image receptor assembly at an opposed end; said C-arm assembly comprising a telescopic straight section to vary a distance of said one end of the C-arm assembly relative to said other end; said straight section including a lock for locking said telescopic section once a distance is selected; said one end of said C-arm assembly including a hinge and a hinge lock;

a control panel comprising a housing including a microprocessor, said microprocessor connected to an on/off switch, digital controls, a kilovoltage level control, an amperage level control, exposure timing circuits, exposure time alarm control including visual and auditory signals, and a LCD panel, said housing including a pedal cable, a hand control cable, and a power supply emerging therefrom, said pedal cable including an activator pedal for use in fluoroscopic mode, said hand control cable including a hand activator control for use in conventional radiographic mode, said housing including a plastic holder for holding said hand control cable when not in use;

three mechanical arms connected to each other, one arm of said three mechanical arms is connected to said control panel, another arm of said three mechanical arms is connected to said housing; said mechanical arms being able to extend, fold and move in various directions;

said intraoral image receptor comprising a fluorescent screen at one end which receives said x-rays after passage through the dental region of the patient, a fiber optic plate coupling which receives an image from said fluorescent screen, a fiber optic cable which transmits said image to said fiber optic connector of said image receptor assembly, and a lead foil backing positioned at an opposed end of said fluorescent screen to reduce radiation exposure to the patient; and a plastic holder device comprising an intraoral image receptor holder and a clip.

13. A method of producing real time images of a dental region of a patient, said method comprising:

(a) selecting a fluoroscopic operating mode on a control panel, (b) emitting x-rays from an emitter for passage through a dental region of a patient;

(c) placing an image receptor opposite said emitter to receive the x-rays after passage thereof through the dental region of the patient to produce a visible light image of said dental region, (d) transmitting said visible light image through a fiber optic system from said image receptor to a charge coupled device to produce a high resolution video signal from said image;

(e) supporting said emitter and said image receptor on a C-arm assembly which is rotatably connected to a housing;

(f) controlling operation from the control panel which is connected to said housing by three mechanical arms which enable the C-arm assembly to be rotatable and also movable in opposite directions along two perpendicular axes so that the emitter and image receptor can be precisely placed at said dental region;

(g) positioning said image receptor and said emitter by a plastic holder on said C-arm assembly; and (h) receiving said video signal to display on a monitor, in real time, the dental region of the patient.

14. The method as claimed in claim 13, comprising operating said emitter at a voltage within a range of 40 to 75 kilovolts and a microamperage between 50 to 300 microamperes.

15. The method as claimed in claim 13, comprising:

placing said emitter and said receptor at the dental region of the patient by moving said C-arm assembly and said housing under the control of said three mechanical arms.

16. The method as claimed in claim 13, wherein:

said positioning of the image receptor with respect to the emitter comprises the steps of unlocking a straight telescoping section of the C-arm assembly, adjusting telescoping of said straight section to adjust spacing of said emitter and said receptor and relocking the straight section.

17. The method as claimed in claim 13, wherein:

said positioning of the image receptor with respect to the emitter comprises the steps of unlocking a hinge lock on one side of the C-arm assembly, pivoting one end of the C-arm assembly by said plastic holder to adjust the position of the image receptor and relocking said hinge lock.

18. The method as claimed in claim 13, comprising:

selecting said fluoroscopic mode by operating a foot control pedal and selectively recording the display on the monitor of the dental region of the patient by operating a second foot control pedal.

19. The method as claimed in claim 13, comprising forming said C-arm assembly as a plurality of connected straight sections.

20. The method as claimed in claim 13, wherein said receptor is formed as a fluoroscopic image receptor to produce said visible image of said dental region or as an intraoral image receptor to produce an X-ray image which is connected by a small fluorescent screen to produce said visible image.

* * * * *